United States Patent [19]

Anton et al.

[11] Patent Number: 5,693,490
[45] Date of Patent: Dec. 2, 1997

[54] PRODUCTION OF GLYCOLATE OXIDASE IN METHYLOTROPHIC YEAST

[75] Inventors: David Leroy Anton; Robert Dicosimo; John Edward Gavagan; Mark Scott Payne, all of Wilmington, Del.

[73] Assignee: E. I. du Pont de Nemours and Company, Wilmington, Del.

[21] Appl. No.: 290,508

[22] Filed: Aug. 15, 1994

Related U.S. Application Data

[63] Continuation-in-part of Ser. No. 25,495, Mar. 3, 1993, abandoned.

[51] Int. Cl.⁶ .......................... C12N 15/29; C12N 15/56; C12N 15/81; C12N 15/09
[52] U.S. Cl. .................. 435/69.1; 435/172.3; 435/320.1; 435/190; 435/254.2; 435/938; 435/254.22; 435/254.23; 536/23.2; 536/23.6; 536/24.1
[58] Field of Search .................................. 536/23.6, 24.1, 536/23.2; 435/69.1, 172.3, 146, 190, 252.3, 938, 254.2, 254.22, 254.23; 530/379; 935/28, 37

[56] References Cited

U.S. PATENT DOCUMENTS

| | | | |
|---|---|---|---|
| 4,808,537 | 2/1989 | Stroman et al. | 435/6 |
| 4,812,405 | 3/1989 | Lair et al. | 435/255 |
| 4,855,231 | 8/1989 | Stroman et al. | 435/68 |
| 4,879,231 | 11/1989 | Stroman et al. | 435/172.3 |
| 4,882,279 | 11/1989 | Cregg | 435/172.3 |

FOREIGN PATENT DOCUMENTS

| | | | |
|---|---|---|---|
| 0 173 378 B1 | 6/1991 | European Pat. Off. | C12N 15/63 |
| A0510693 | 10/1992 | European Pat. Off. | C12N 15/80 |

OTHER PUBLICATIONS

N. E. Tolbert et al., *J. Biol. Chem.* 181:905 (1949).
Tolbert, N.E. et al, *J. Biol. Chem.*, 181, 905–914 (1949).
Volokita, M. et al, *J. Biol. Chem.*, 262(33), 15825–15828 (1987).
Macheroux, P. et al, *Biochemistry*, 30, 4612–4619 (1991).
Macheroux, P. et al, *Biochem. Biophys. Acta.*, 1132, 11–16 (1992).
Lindqvist, Y. et al, *Proc. Nat'l Acad. Sci. USA*, 82, 6855–6859 (1985).
Haber et al., Methylotrophic Bacteria: Biochemical Diversity and Genetics, *Science*, 221, 1147, Sep. 16, 1983.
Tschopp et al., Expression of the Lacz Gene From Two Methanol–Regulated Promoters in Pichia pastoris, *Nucleic Acids Research*, 15, No. 9, 3859–3876, 1987.
Harder et al., Methylotrophic Yeasts, *Yeast Biotechnology and Biocatalysis*, 395–396.
Ratner, Mark, Protein Expression in Yeast, *Biotechnology Nature Publishing*, 7, No. 11, 1129–1133, Nov. 1982.
W. Harder, Structure/Function Relationships in Methylotrophic Yeasts, *FEMS Microbiology Reviews*, 87, 191–200, 1990.
Hanne et al., Degradation and Induction Specificity in Actnomycetes That Degrade p–Nitrophenol, *Applied and Environmental Microbiology*, 59, No. 10, 3505–3508, Oct. 1993.
Lindqvist et al 1985 Proc Natl Acad Sci USA 82:6855–6859.
Hanne et al 1993 (Oct.) Applied and Environ Microbiol 59(10):3505–3508.
Cregg et al 1993 (Aug.) Bio/Technology 11:905–910.
Ratner 1989 Bio/Technology 7: 1129–1133.
Sreekrishna 1993 In Industrial Microorganisms: Basic and Applied Molecular Genetics; Baltz et al (eds); Am Soc Microbiol (publ) pp. 119–126.

*Primary Examiner*—David T. Fox
*Assistant Examiner*—Thomas Haas

[57] ABSTRACT

Methylotrophic yeast have been transformed with a heterologous gene encoding glycolate oxidase. The transformed methylotrophic yeast are useful as a catalyst for transforming glycolate to glyoxylate.

16 Claims, 6 Drawing Sheets

FIG. 1

```
  1 MEITNVNEYE AIAKQKLPKM VYDYYASGAE DQWTLAENRN AFSRILFRPR
 51 ILIDVTNIDM TTTILGFKIS MPIMIAPTAM QKMAHPEGEY ATARAASAAG
101 TIMTLSSWAT SSVEEVASTG PGIRFFQLYV YKDRNVVAQL VRRAERAGFK
151 AIALTVDTPR LGRREADIKN RFVLPPFLTL KNFEGIDLGK MDKANDSGLS
201 SYVAGQIDRS LSWKDVAWLQ TITSLPILVK GVITAEDARL AVQHGAAGII
251 VSNHGARQLD YVPATIMALE EVVKAAQGRI PVFLDGGVRR GTDVFKALAL
301 GAAGVFIGRP VVFSLAAEGE AGVKKVLQMM RDEFELTMAL SGCRSLKEIS
351 RSHIAADWDG PSSRAVARL
```

M: DNA molecular size markers
1: GTS115 PCR
2: MSP10 PCR
3: MSP12 PCR
4: pMP1 PCR

PRODUCTION OF GLYCOLATE OXIDASE IN METHYLOTROPHIC YEAST

This is a continuation-in-part of application Ser. No. 08/025,495 filed Mar. 3, 1993, now abandoned.

FIELD OF INVENTION

The present invention relates to the production of enzymatically-active glycolate oxidase from a recombinant yeast. More specifically, the invention relates to culturing a transformant of a methylotrophic yeast species containing a DNA fragment coding for the expression of glycolate oxidase.

BACKGROUND

Glyoxylic acid is an important intermediate in the manufacture of various agrochemicals, pharmaceuticals and fragrances. Typical commercial production of glyoxylic acid employes either oxidation chemistry or electrochemical means. Electrochemical manufacture involves either the reduction of oxalic acid or the anodic oxidation of glyoxal to form glyoxylic acid whereas chemical oxidation generally involves the oxidation of glyoxal in the presence of a strong acid such as $HNO_3$. A consequence of these commercial processes is the production of waste streams containing various toxic acids and heavy metals. Increased public concern coupled with mounting government regulations surrounding the production of toxic wastes has provided impetus for a search for an alternative, cost effective, yet environmentally acceptable method of glyoxylic acid production. One such potential route lies in microbially-mediated enzymatic catalysis involving the oxidation of glycolic acid by glycolate oxidase.

Glycolate oxidase is an enzyme available from various sources, including green leafy plants and mammalian cells. N. E. Tolbert et al., *J. Biol. Chem.*, 181:905 (1949), first reported an enzyme, extracted from tobacco leaves, which catalyzed the oxidation of glycolic acid to formic acid and $CO_2$ via the intermediate formation of glyoxylic acid. Similarly, K. E. Richardson and N. E. Tolbert, *J. Biol. Chem.*, 236:1280 (1961), reported the formation of oxalic acid during the glycolate oxidase-catalyzed oxidation of glycolic acid to glyoxylic acid, using enzymes isolated from tobacco, sugar beet, Swiss chard, spinach, or rat liver. C. O. Clagett et al., *J. Biol. Chem.*, 78:977 (1949), reported that the optimum pH for the glycolate oxidase catalyzed oxidation of glycolic acid with oxygen was about 7.8–8.6, and the optimum temperature was 35°–40° C.

Recent advances in recombinant DNA technology, combined with the isolation of cDNA coding for the spinach enzyme (see Volokita et al, *J. Biol. Chem.*, 262(33):15825 (1987)) have allowed for the construction of microbial strains that are intended to serve as alternative, economic enzyme sources. To date the host organism of choice for expression of heterologous proteins in commercial applications has been *Escherichia coli*. However in some situations *Escherichia coli* may prove to be an unsuitable host. For example, *Escherichia coli* contains a number of toxic pyrogenic and proteolytic factors that may interfere with the activity of the expressed enzyme. These and other considerations have led to increased interest in alternative hosts, in particular, yeasts for the production of active enzymes.

Yeasts offer several advantages to commercial applications over *Escherichia coli* and other bacteria. Yeasts can generally be grown to higher densities than bacteria and are readily adaptable to continuous fermentation processing. It has been reported, for example, that *Pichia pastoris* can be grown to cell densities in excess of 100 g/l (U.S. Pat. No. 4,414,329). Additional advantages of yeast hosts include the fact that many critical functions of the organism, such as oxidative phosphorylations, are located within organelles and thus are not exposed to the possible deleterious effects of the organism's over-expression of foreign enzymatic products. Furthermore, yeasts appear to be capable of glycosylation of expressed polypeptide products where such glycosylation is important to the bioactivity of the polypeptide product.

Unfortunately, despite their having the genetic capacity to produce glycolate oxidase, the microbial hosts used to date have performed poorly, producing either inactive enzyme, or producing the enzyme at very modest levels. Although early data indicated that *Escherichia coli* was unable to produce glycolate oxidase in enzymatically-active form following introduction of the enzyme-encoding gene in expressible form (see Macheroux et al., *Biochem.*, 30:4612 (1991)), it has since been determined that active enzyme could indeed be expressed in this host using a T7 RNA polymerase promoter, albeit in very modest amounts (Macheroux et al., *Biochem. Biophys. Acta.*, 1132:11 (1992)). It has been possible to achieve expression of active glycolate oxidase from various species of fungi including those of the genus Aspergillus (U.S. Ser. No. 07/817,170) and Saccharomyces (Macheroux et al., *Biochem.*, 30:4612 (1991)) however these hosts have only been capable of producing enzymes at levels far below what would be considered commercially useful. There exists a need, therefore, for a cost effective source of glycolate oxidase in commercially useful quantities.

SUMMARY OF THE INVENTION

It is the object of the present invention to provide a DNA fusion for the expression of enzymatically-active glycolate oxidase comprising a first DNA fragment encoding a suitable promoter from a methylotrophic yeast, operably and expressibly connected to a second DNA fragment encoding a glycolate oxidase gene. Optionally said DNA fusion may also comprise a third DNA fragment encoding a suitable signal peptide for the optional secretion of glycolate oxidase into the growth medium.

The present invention further provides a transformed methylotrophic yeast for the expression of enzymatically-active glycolate oxidase containing a heterologous DNA fusion capable of expressing glycolate oxidase.

In another embodiment of the invention a transformed yeast is provided which co-expresses enzymatically-active endogenously produced catalase with enzymatically-active glycolate oxidase.

Additionally a transformed yeast is provided wherein said yeast secretes glycolate oxidase into the growth medium.

The present invention provides a process for the production of enzymatically-active glycolate oxidase comprising the steps of culturing a transformed methylotrophic yeast containing a heterologous DNA construct encoding enzymatically-active glycolate oxidase and maintaining the growth of said yeast under conditions suitable for the maximal production of glycolate oxidase. Optionally, a method is also provided where endogenously produced catalase is co-expressed with said glycolate oxidase.

BRIEF DESCRIPTION OF THE DRAWINGS BIOLOGICAL DEPOSITS AND SEQUENCE LISTINGS

FIG. 1 illustrates the amino acid sequence of spinach glycolate oxidase (SEQ ID NO.: 3).

Figure 2:
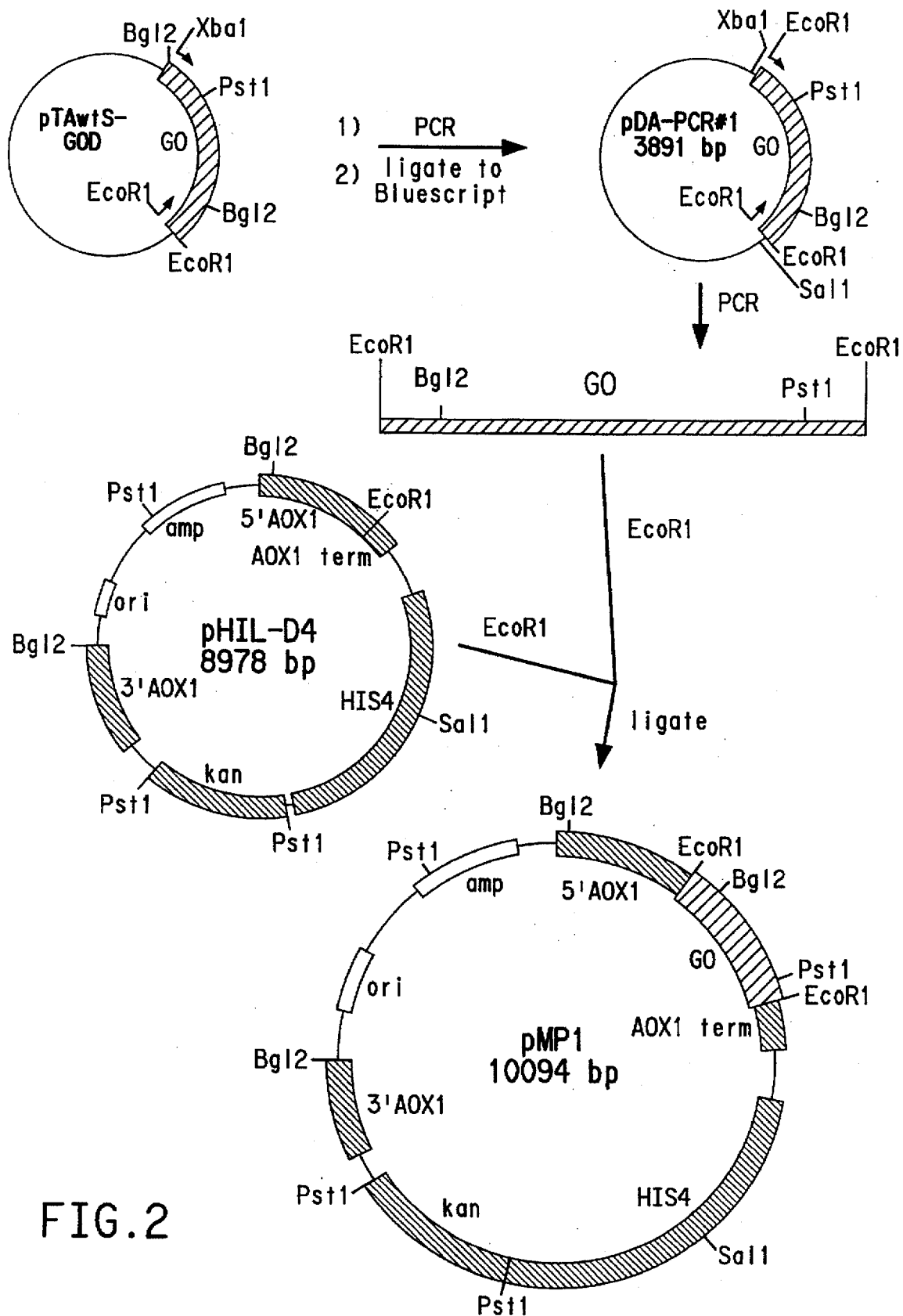
FIG. 2 illustrates the creation of plasmid pMP1 from plasmids pHIL-D4 and pDA-PCR#1.

Applicants have provided sequence listings 1–3 in conformity with 37 C.F.R. 1.821–1.825 and Appendices A and B ("Requirements for Application Disclosures Containing Nucleotides and/or Amino Acid Sequences").

Applicants have made the following biological deposits under the terms of the Budapest Treaty:

| Depositor Identification Reference | Int'l. Depository Designation | Date of Deposit |
|---|---|---|
| Pichia pastorius (MSP12) | NRRL Y-21040 | 28 December 1992 |
| Pichia pastorius (MSP10) | NRRL Y-21001 | 24 September 1992 |
| Hansenula polymorpha | NRRL Y-21065 | 30 March 1993 |
| pMP1 (MSP001) | NRRL B-21292 | 29 June 1994 |

As used herein, "NRRL" refers to the Northern Regional Research Laboratory, Agricultural Research Service Culture Collection international depository located at 11815 N. University Street, Peoria, Ill. 61604 U.S.A. The "NRRL No." is the accession number to cultures on deposit at the NRRL.

DETAILED DESCRIPTION OF THE INVENTION

The following definitions are used herein and should be referred to for claim interpretation.

The terms "promoter" and "promoter region" refer to a sequence of DNA, usually upstream of (5" to) the protein coding sequence of a structural gene, which controls the expression of the coding region by providing the recognition for RNA polymerase and/or other factors required for transcription to start at the correct site. Promoter sequences are necessary but not always sufficient to drive the expression of the gene.

The term "fragment" refers to a fraction of the DNA sequence of the particular region.

The term "nucleic acid" refers to a molecule which can be single stranded or double stranded, composed of monomers (nucleotides) containing a sugar, phosphate and either a purine or pyrimidine. In bacteria and in higher plants, "deoxyribonucleic acid" (DNA) refers to the genetic material while "ribonucleic acid" (RNA) is involved in the translation of the information from DNA into proteins.

The terms "regulation" and "regulate" refer to the modulation of gene expression controlled by DNA sequence elements located primarily, but not exclusively upstream of (5' to) the transcription start of a gene. Regulation may result in an all or none response to a stimulation, or it may result in variations in the level of gene expression.

The term "coding sequence" refers to that portion of a gene encoding a protein, polypeptide, or a portion thereof, and excluding the regulatory sequences which drive the initiation of transcription. The coding sequence may constitute an uninterrupted coding region or it may include one or more introns bounded by appropriate splice junctions. The coding sequence may be a composite of segments derived from different sources, naturally occurring or synthetic.

The term "construction" or "construct" refers to a plasmid, virus, autonomously replicating sequence, phage or nucleotide sequence, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "transformation" refers to the acquisition of new genes in a cell after the incorporation of nucleic acid.

The term, "operably linked" refers to the chemical fusion of two fragments of DNA in a proper orientation and reading frame to be transcribed into functional RNA.

The term "expression" refers to the transcription and translation to gene product from a gene coding for the sequence of the gene product. In the expression, a DNA chain coding for the sequence of gene product is first transcribed to a complimentary RNA which is often a messenger RNA and, then, the thus transcribed messenger RNA is translated into the above-mentioned gene product if the gene product is a protein.

The term "translation initiation signal" refers to a unit of three nucleotides (codon) in a nucleic acid that specifies the initiation of protein synthesis.

The term "plasmid" refers to an extra-chromosomal element often carrying genes which are not part of the central metabolism of the cell, and usually in the form of circular double-stranded DNA molecules.

The term "restriction endonuclease" refers to an enzyme which binds and cuts within a specific nucleotide sequence within double-stranded DNA.

The term "signal peptide" refers to an amino terminal polypeptide preceding the secreted mature protein. The signal peptide is cleaved from and is therefore not present in the mature protein. Signal peptides have the function of directing and translocating secreted proteins across cell membranes. Signal peptide is also referred to as signal protein.

The term "mature protein" refers to the final secreted protein product without any part of the signal peptide attached.

The term "compatible restriction sites" refers to different restriction sites that when cleaved yield nucleotide ends that can be ligated without any additional modification.

The term "suitable promoter" refers to any eukaryotic or prokaryotic promoter capable of driving the expression of the glycolate oxidase gene in a host cell.

The term "suitable termination sequence" refers to any eukaryotic or prokaryotic termination sequence capable of terminating the transcription of the glycolate oxidase gene in a host cell.

The designation "NRRL" refers to the U.S. Department of Agriculture, Northern Regional Research Laboratories, located 1815 No. University Street in Peoria, Ill., and the "NRRL No." is the accession number to cultures on deposit at the NRRL.

The term "enzymatically-active glycolate oxidase" refers to glycolate oxidase in a form capable of converting glycolate to glyoxylate as determined by assays of conventional design. It will be understood that the term will also encompass enzyme contained within vesicles such as inclusion bodies where the enzyme must be isolated and renatured in order to catalyze the glycolate to glyoxylate reaction.

The term "international unit" abbreviated as "IU" refers to units of enzymatic activity and is defined as the amount of enzyme that will catalyze the transformation of one micromole of substrate per minute.

The term "methylotrophic yeast" refers to those yeast genera capable of utilizing methanol as a carbon source for the production of the energy resources necessary to maintain cellular function and containing a gene for the expression of methanol oxidase. Typical methylotrophic yeast include members of the genera Pichia, Hansenula, Torulopsis, Candida, and Karwinskia. These yeast genera can use methanol as a sole carbon source. The invention specifically excludes yeast such as Saccharomyces which are unable to use carbon as a sole energy source.

The invention of the present application relates to the production of enzymatically-active glycolate oxidase by yeasts of the genus Pichia in commercially-useful quantities.

The glycolate oxidase of the present invention may have a structure corresponding to any naturally occurring form of the enzyme, or may have a genetically engineered variant structure, provided however that enzymatically-active glycolate oxidase, as defined above, is retained. Naturally occurring forms of glycolate oxidase include, for example, spinach-produced glycolate oxidase. As shown in FIG. 1 herein, spinach glycolate oxidase consists, in its mature form, of 369 amino acids arranged in the indicated sequence. According to a preferred embodiment of the present invention, the glycolate oxidase is spinach glycolate oxidase or an enzymatically-active variant of spinach glycolate oxidase, e.g., a enzymatically-active fragment of the enzyme, or an analogue in which one or more amino acids is replaced using conservative amino acid replacements, or a variant in which the region of the enzyme which directs its peroxisomal accumulation is deleted. See Macheroux et al. (1991), supra.

The present invention employs as host for glycolate oxidase production any of the species and varieties of the class of methylotrophic yeasts. Suitable hosts include those of the genera Pichia, Hansenula, Torulopsis, Candida, and Karwinskia where Pichia is preferred. Particularly suitable species of Pichia, include *Pichia pastoris* and the closely related *P. stipitis, P. ohmeri, P. caribaea, P. guilliermondii, P. ciferri, P. kluyveri*, and *P. pinus* where *Pichia pastoris* is most preferred.

One class of useful Pichia hosts are auxotrophic mutants, i.e., mutant strains which require supplementation with one or more amino acids, vitamins or other nutrients in order to grow. Transformation of such mutants can be readily selected by employing, as part of the recombinant DNA material used to transform the mutant host, DNA sequences which code for the production of the missing gene product. A preferred host yeast strain is *Pichia pastoris* GTS115 (his4), which is a mutant defective in the ability to produce histidine, and has been identified as having the mutant genotype his4. *Pichia pastoris* GTS115 (his4), has been deposited with the Northern Regional Research Laboratories, (NRRL) under the terms of the Budapest Treaty and will be hereinafter referred to by it's NRRL accession number NRRL Y-15851. It is recognized by those of skill in the art that mutants in many other genes important in Pichia metabolism also exist or can be isolated and therefore virtually any other auxotrophic Pichia host would be suitable for the purpose of the present invention.

A variety of genetic constructs, adapted to receive heterologous DNA and to control DNA expression, have been developed for use with Pichia hosts and any of these may be employed for the purpose of producing glycolate oxidase in the Pichia host. Such genetic constructs, conventionally referred to as expression cassettes, comprise a region 5' of the heterologous DNA insert which harbors transcriptional initiation controls, and a region 3' of the DNA insert which controls transcriptional termination. It is preferred to derive both control regions from genes homologous to Pichia. However, such control regions need not be derived from the genes native to the species chosen as the host, or derived from the same Pichia gene.

Initiation control regions, more commonly referred to as promoters, which are useful to drive expression of glycolate oxidase-encoding DNA, include those derived from genes in the methanol utilization pathway of Pichia. Virtually any Pichia promoter capable of driving the spinach glycolate oxidase gene is suitable for the present invention including glyceraldyhyde-3-phosphate dehydrogenase and dihydroxy acetone synthase however the preferred promoter is the alcohol oxidase promoter, AOX1.

Termination control regions, which may include a polyadenylation site and regions functional to terminate transcription, may also be derived from various genes native to Pichia hosts, or optionally other yeast hosts or even from higher plants. Optionally a Pichia polyadenylation termination site may be unnecessary. However, a genetic construct which includes a Pichia polyadenylation termination site is preferred.

For intracellular production of glycolate oxidase, DNA encoding glycolate oxidase is linked operably through its initiation codon to the selected expression control region, such that expression results in the formation of glycolate oxidase-encoding messenger RNA. Alternatively, if production of a glycolate oxidase fusion protein is desired, DNA encoding for glycolate oxidase is linked at its 5' end to the 3' end of the gene encoding the carrier protein. Optionally the reverse orientation could be constructed where DNA encoding the carrier protein is linked at its 5' end to the 3' end of the DNA encoding glycolate oxidase. Also, if desired, DNA coding for an enzyme clearable linker is incorporated without reading frame disruption, between the oxidase-encoding DNA and the carrier-encoding DNA, so that expression yields a fusion protein from which glycolate oxidase can be liberated by enzyme cleavage. An example of the fusion protein approach to protein production is provided by Contreras et al., *Bio Technology*, 9:378 (1991).

The construction of an expression cassette for the expression of glycolate oxidase in Pichia may be accomplished by means well known to those skilled in the art. The source of the glycolate oxidase gene may either be chromosomal DNA or a previously constructed vector containing the gene. Generally it is preferred to isolate the glycolate oxidase gene from an existing vector. It is also preferred that the glycolate oxidase gene be bounded on both the 5' and 3' ends by convenient restrictions sites. Any vector or plasmid containing a suitable glycolate oxidase gene may be used, including the chromosomal copy. However, for the purpose of the present invention the plasmid pDA-PCR#1 is preferred. pDA-PCR#1 is derived from the Aspergillus transformation plasmid pTAwtS-GOD. Plasmid pTAwtS-GOD contains a spinach glycolate oxidase gene under the control of a *Aspergillus nidulans* alcA promoter and bounded at the 5' end by a BglII site and at the 3' end by an EcoRI site, (FIG. 2). The glycolate oxidase gene in pTAwtS-GOD was amplified by conventional PCR protocols using primers which incorporated an XbaI site at one end and an EcoRI site ar the opposite end. The PCR fragment was ligated between the XbaI and EcoRI sites in the Bluescript plasmid (Stratagene, La Jolla, Calif.) to give the plasmid pDA-PCR#1.

Isolated DNA encoding the glycolate oxidase protein is optionally amplified by techniques well known in the art for the purpose of cloning into a suitable Pichia transformation vector. Any method of amplification may be used including Polymerase Chain Reaction (PCR) or Ligase Chain Reaction (LCR) where PCR is most preferred. Amplified glycolate oxidase DNA is then cloned into a suitable Pichia transformation vector. A number of transformation vectors are suitable where the vector contains a promoter capable of driving the glycolate oxidase gene and where the promoter contains, downstream, a restriction site compatible with the restriction sites flanking the glycolate oxidase gene. Any suitable transformation vector may be used, including pHIL-A1, pHIL-D1, pHIL-D2, pHIL-D3, pHIL-D5, pHIL-S1, pRK20, and pT76H4, however plasmid pHIL-D4 is most preferred. pHIL-D4 is commercially available from Phillips Corp. (Phillips Petroleum Company, Bartlesville, Okla.) and is described in detail in FIG. 2. Briefly, pHIL-D4 includes the following features (i) *Pichia pastoris* methanol inducible promoter AOX1 linked through an EcoRI site to (ii) AOX1 transcriptional termination element, (iii) a *P. pastoris* selectable marker HIS4; (iv) a kanamycin resistance gene; (v) a 3' AOX1 flanking fragment; (vi) and pBR322 elements enabling propagation and selection in *E. coli* hosts. The HIS4 p marker is useful in selecting for positively transformed hosts and the kanamycin resistance gene is useful for selecting high copy number transformants. Cloning of the glycolate oxidase DNA is accomplished by restriction enzyme digestion of the vector and the glycolate oxidase containing DNA fragment with compatible restriction endonucleases, followed by a ligation according to protocols well known to those skilled in the art. Typically the result of such ligation is the creation of a vector in which the spinach glycolate oxidase gene is inserted between the AOX1 promoter and the AOX1 termination region. The resulting vector is capable of transforming any suitable *Pichia sp.* and effecting the expression of enzymatically-active glycolate oxidase and has been labeled pMP1.

Because the plasmid pMP1 lacks an origin of replication for Pichia, all transformants arise from chromosomal integration of the plasmid. One skilled in the art will recognize, however, that a suitable transforming plasmid could also be constructed to be autonomously replicating within the transformed host. For the purpose of the present invention chromosomal integration of the plasmid is preferred, as it provides a more stable transformed host.

Transformation of a *Pichia sp.* host may be accomplished by a variety of protocols well known in the art. As previously mentioned, preferred Pichia hosts comprise Pichia auxotrophic mutants and most preferred is the His$^-$ mutant, GTS115 (his4) (NRRL Y-15851). Briefly, spheroplasts of the host strain GTS115 (his4) are first prepared using a yeast cell wall degrading enzyme followed by incubation with the transformation vector, pMP1. After plating on selective media, His$^+$ transformants are isolated. His$^+$ transformants may be further screened for specific replacement of chromosomal alcohol oxidase gene by glycolate oxidase gene by selecting for a slow growing phenotype on methanol (Mut$^-$). For the purpose of producing commercially useful quantities of glycolate oxidase it is advantageous to select clones with the highest possible copy number of the transforming plasmid. This is accomplished by growing the Kan$^+$ transformants in the presence of ever increasing levels of kanamycin and selecting the clones with the greatest tolerance to kanamycin.

Transformants, containing multiple copies of the glycolate oxidase gene under the control of the Pichia alcohol oxidase promoter are then evaluated for the production of enzymatically-active glycolate oxidase. Transformants are grown, according to standard techniques. Briefly, cells are grown to an $A_{600}$ of 2–10 in MGY medium with shaking at 30° C. Cells are then pelleted and resuspended in MM medium containing 0.5% methanol for induction and incubated with shaking at 30° C. for 1–4 days. Glycolate oxidase protein may be detected by Western blot analysis or glycolate oxidase activity may be detected by means of a spectrophotometric assay. Most preferred is the method described by Soda et al., *Agr. Biol. Chem.*, 37(6):1393 (1973). The Soda et al. assay measures the glyoxylate produced by the glycolate oxidase-catalyzed oxidation of glycolate by reacting the glyoxylate with glycine and o-aminobenzaldehyde to form a yellow complex having an absorbance maximum at 440 nm.

Optionally it may be desired to produce active glycolate oxidase as a secretion product of the transformed yeast host. Secretion of desired proteins into the growth media has the advantages of simplified and less costly purification procedures. It is well known in the art that secretion signal sequences are often useful in facilitating the active transport of expressible proteins across cell membranes. The creation of a transformed Pichia capable of glycolate oxidase secretion may be accomplished by the incorporation of a DNA sequence that codes for a secretion signal which is functional in the Pichia production host. The secretion signal DNA is inserted on the expression cassette, between the expression-controlling DNA and the oxidase-encoding DNA, and in reading frame with the latter. To create a Pichia host capable of glycolate oxidase secretion, the secretion vector, pHIL-S1 (Phillips Petroleum Company, Bartlesville, Okla.) may be used. The Phillips integrative/secretion vector pHIL-S1 (FIG. 6) is very similar to pHIL-D4 (FIG. 2) with the exception that a DNA fragment encoding the *P. pastoris* acid phosphatase (PHO1) secretion signal followed by a short multiple cloning segment has been inserted between the 5'AOX1 fragment and the AOX1 termination fragment. Transformation of the Pichia host may be accomplished by subcloning the glycolate oxidase gene (isolated as described above from pDA-PCR#1) at the multiple cloning site in frame with the secretion signal sequence. Such a vector may then be used to transform a suitable Pichia host (such as GTS115) in a manner analogous to that described above for pHIL-D4.

Transformants of Pichia hosts which co-express glycolate oxidase and catalase are useful for the manufacture of glyoxylic acid from glycolic acid (hydroxyacetic acid). Although the enzyme-catalyzed reaction of glycolic acid with oxygen has been known for many years, high selectivities (>99%) to glyoxylic acid have not been previously obtained, nor has the oxidation of glycolic acid been performed at concentrations of 0.20M to 2.5M. A U.S. patent application Ser. No. 07/422,011, filed Oct. 16, 1989, "Production of Glyoxylic Acid from Glycolic Acid", describes a process for the enzymatic conversion of glycolic acid to glyoxylic acid in the presence of oxygen, and the soluble enzymes glycolate oxidase and catalase. This process also demonstrates the unexpected synergistic effect of using both catalase (to destroy by-product hydrogen peroxide) and an amine buffer capable of forming a chemical adduct with the glyoxylic acid produced (limiting its further oxidation). Neither the separate addition of catalase or an amine buffer were found to produce the high selectivity observed when both were present. Further, the almost quantitative yields of glyoxylic acid obtained were more than expected from a simple additive effect of using catalase or amine buffer alone. An improvement to the above process utilizes a whole microbial cell as a catalyst, in place of the soluble enzymes. The whole cell catalyzed process is fully described in the previously filed U.S. patent application Ser. No. 07/817,165.

The previously reported use of soluble enzymes as catalysts for the production of glyoxylic acid poses several problems. 1) Catalyst recovery for reuse is not easily performed. 2) Enzyme activity is not as stable as with immobilized enzyme or whole cell catalyst systems. 3) Soluble glycolate oxidase is not stable to the sparging of the reaction mixture with oxygen. Oxygen is required to increase the rate of oxygen dissolution and, thus, reaction rate. A second related U.S. patent application Ser. No. 07/817,170, filed Jan. 6, 1992, "Glycolate Oxidase Production", described the construction of several transformants of *Aspergillus nidulans* which express the glycolate oxidase from spinach as well as an endogenous catalase. Several advantages for the use of these whole-cell catalysts over the use of soluble enzymes for the production of glyoxylic acid in the present invention are:

(1) the whole-cell catalysts are easily recovered from the reaction mixture at the conclusion of the reaction for reuse, whereas the soluble enzyme is only recovered with great difficulty and loss of activity, (2) they are more stable than the soluble enzyme, both for the number of catalyst turnovers obtained versus the soluble enzyme, as well as for recovered enzyme activity at the conclusion of a reaction; and (3) most importantly, they are stable to reaction conditions where oxygen or an oxygen-containing gas is sparged into the reaction mixture to increase the rate of oxygen dissolution and reaction rate, where under similar reaction conditions the soluble glycolate oxidase is rapidly denatured.

The present invention provides a transformed methylotrophic yeast host capable of expressing both a heterologous glycolate oxidase gene and an endogenous catalase gene. It is well known in the art that all methylotrophic yeast have some capacity to produce endogenous catalase, however, members of the genera Pichia, and Hansenula, are preferred. *Pichia pasotris* strains were evaluated for their ability to produce endogenous catalase and *P. pastoris* GTS115 was selected. For the evaluation of catalase production transformed *Pichia pastoris* GTS115 (his4), (NRRL Y-15851), was grown according to the procedure described above and analyzed for enzymatically-active catalase. Several methods of determining catalase activity are available.

Expression of enzymatically active glycolate oxidase through use of the method which is the subject matter of this invention can reasonably be expected to be as high as 6800 IU glycolate oxidase(active)/gram dry cell weight. This level is reasonable in light of various heterologous proteins expressed in Pichia at concentrations of up to 80% of total protein. These include invertase, human epidermal growth factor, and mouse epidermal growth factor (see Cregg et al., Bio/Technology, vol. 11, pp. 905–910 (1993)). Applicants have produced 432 IU/gram blotted wet cell weight of active glycolate oxidase in MSP10 (see Example 3). Lyophilization of blotted wet cells of yeast transformants generally yields approximately 30% dry cell weight relative to the original blotted cell weight. Accordingly, 1 IU of glycolate oxidase activity per gram wet cell weight is equivalent to 3.33 IU/gram dry cell weight. Therefore, Applicants' 432 IU/g blotted cell weight corresponds to 1440 IU/g dry cell weight. This activity level is equivalent to 17% to 22% of total protein. Extrapolation in light of the above mentioned work by Cregg et al. produces the 6800 IU level.

Materials and Methods

The plasmids pHIL-D4 and pHIL-S1 were obtained from the Phillips Company (Phillips Petroleum Company, Bartlesville, Okla.). PCR reagents were obtained from and used according to Perkin-Elmer Cetus. Protocols conventional to PCR were employed as described in Innis, M. et al., PCR Protocols, 1990, Academic Press. Restriction enzyme digestions, ligations transformations and plasmid preparations were done as described in Sambrook, J. et al., Molecular Cloning: a laboratory manual, 1989, Cold Spring Harbor Laboratory Press.

The following non-limiting examples are meant to illustrate the invention but are not meant to limit it in any way.

EXAMPLES

Example 1

Construction of Plasmid pMP1 Containing Spinach Glycolate Oxidase Gene

For the construction of a vector capable of transforming *Pichia sp.* for the expression of glycolate oxidase, the glycolate oxidase (GO) gene located in the vector pDA-PCR#1 (FIG. 2) was used. pDA-PCR#1 is derived from the Aspergillus transformation plasmid pTAwtS-GOD shown in FIG. 2. Briefly, pTAwtS-GOD contains a spinach glycolate oxidase gene under the control of a *Aspergillus nidulans* alcA promoter and bounded at the 5' end by a BglII site and at the 3' end by an EcoRI site. The glycolate oxidase gene in pTAwtS-GOD was amplified by conventional PCR protocols using primers which incorporated an XbaI site at one end and an EcoRI site at the opposite end. The PCR fragment was ligated between the XbaI and EcoRI sites in the Bluescript plasmid (Stratagene, La Jolla, Calif.) to give the plasmid pDA-PCR#1 (FIG. 2)

The GO gene as found in pDA-PCR#1 was amplified by polymerase chain reaction (PCR) using primers incorporating EcoRI restriction sites (MP18: 5' TAC CGA ATT CAT GGA GAT CAC AAA TGT G 3' (SEQ ID NO.: 1) and MP19: 5' AAC AGA ATT CTT ATA ATC TGG CAA CAG A 3' (SEQ ID NO.: 2)).

Plasmid pHIL-D4 is commercially available from Phillips Co. (Phillips Petroleum Company, Bartlesville, Okla.) and is a shuttle vector designed for integration in *Pichia pastoris*. Briefly, this vector incorporates a 1100 bp methanol inducible promoter AOX1 which is connected through an EcoRI site to a 300 bp AOX1 transcriptional termination element. Also on the plasmid are a *P. pastoris* selectable marker HIS4, a kanamycin resistance gene, a 3' AOX1 flanking fragment and elements allowing propagation and selection in *E. coli* hosts (FIG. 2).

The amplified GO gene was digested with EcoRI and subcloned into pHIL-D4 at the EcoRI site (between AOX1 promoter and AOX1 termination) in the forward orientation to produce plasmid pMP1 (FIG. 2). pMP1 was then used to transform *Pichia pastoris*.

Example 2

Transformation of *Pichia pastoris* with pMP1

A host strain of Pichia pastoris designated GTS115 (his4), (Phillips Petroleum Company, Bartlesville, Okla.) was selected for transformation by pMP1. pMP1 was introduced into GTS115 (his4) using conventional DNA-mediated

11 transformation protocols described by Phillips. Cregg et al., *Mol. Cell. Biol.*, 5(12):3376 (1985).

Figure 3:
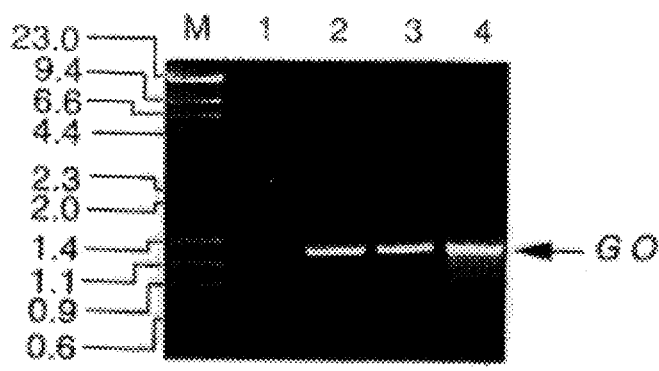
FIG. 3 is a gel electrophoresis of PCR detection of the glycolate oxidase gene from strains MSP10 and MSP12.

Spheroplasts of the host strain GTS115 were first prepared using the cell wall degrading enzyme zymolase (Sigma Chemical, St. Louis, Mo.). Spheroplasts were then incubated in the presence of sorbitol/polyethylene glycol, with about 1–2 µg of linearized pMP1. Transformants were allowed to regenerate on media selective for His+ prototrophs. His+ clones were screened for chromosomal AOX1 displacement by replica plating on media with or without 0.5% methanol and selecting clones with a slow growing phenotype on methanol (Mut−). Mut− clones were further screened for expression cassette copy number by selective growth in media containing increasing levels of kanamycin (from 100 µg/ml to 1000 µg/ml). Two clones exhibiting the greatest resistance to kanamycin were selected and labeled MSP10 and MSP12. MSP10 and MSP12 tolerated >1000 µg/ml kanamycin whereas 15 other His+/Mut− clones did not grow in kanamycin >100 µg/ml. PCR with primers MP18 (SEQ ID NO.: 1) and MP19 (SEQ ID NO.: 2) of chromosomal DNA isolated from MSP10 and MSP12 resulted in a 1.1 kb fragment indicating the presence of GO gene in these recombinant strains and indicated in FIG. 3.

Example 3

Expression of Active Glycolate Oxidase from MSP10 and MSP12

Figure 4:
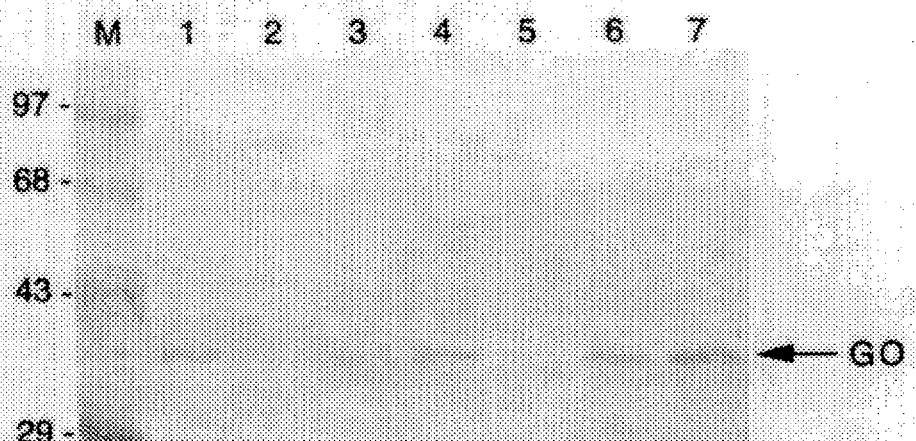
FIG. 4 is a Western blot analysis of glycolate oxidase protein production from transformed strains MSP10 and MSP12.

Strains MSP10 and MSP12 harboring multiple copies of the glycolate oxidase gene were evaluated individually for glycolate oxidase activity. This was done by growing MSP10 and MSP12 in appropriate media followed by induction with 0.5% methanol. Cells are grown to an $A_{600}$ of 2–10 in MGY medium (1.34% yeast nitrogen base without amino acids, 0.00004% biotin, 1% glycerol) with shaking at 30° C. Cells are then pelleted and resuspended in MM medium (1.34% yeast nitrogen base without amino acids, 0.00004% biotin, 0.5% methanol) and incubated with shaking at 30° C. for 1–4 days. Cells were harvested at 0, 3.5 and 24 hrs post induction and lysed by vortexing with an equal volume of 0.5 mm glass beads in 50 mM sodium phosphate pH 7.4, 1 mM PMSF, 1 mM EDTA, 5% glycerol and 0.01 mM FMN for a total of 4 min in increments of 30 sec followed by 30 sec on ice. Detection of GO enzyme by western blot analysis of these lysates confirmed the expression of GO gene in these strains (FIG. 4).

Figure 5:
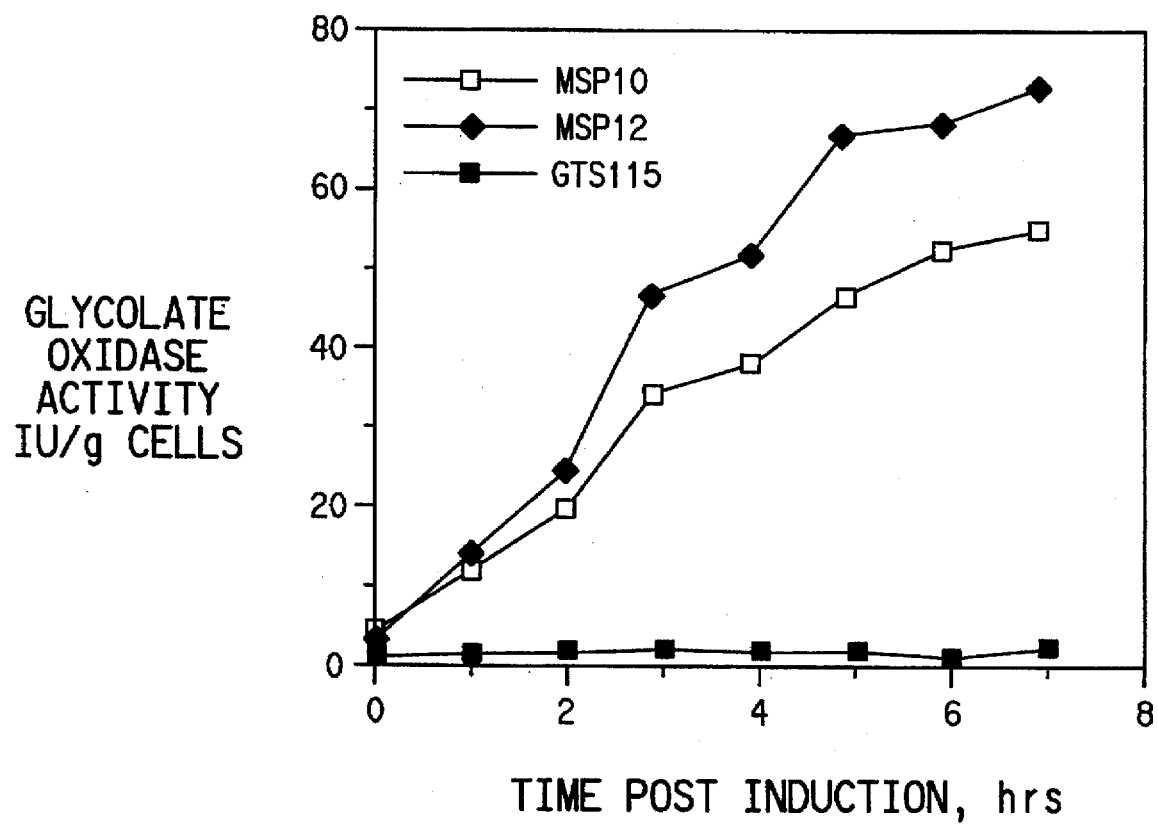
FIG. 5 is a graphic representation illustrating glycolate oxidase activity from induced cultures of transformed strains MSP10 and MSP12.

Glycolate oxidase activity was measured from cell lysates using a spectrophotometric assay (with absorbance monitoring at 440 nm) for GO enzyme activity employing o-aminobenzaldehyde and glycine (K. Soda, *Agr. Biol. Chem.*, 37:1393 (1973)) which demonstrated activities of 100–450 IU/g blotted cells. FIG. 5 illustrates a representative time course of glycolate oxidase activity after induction by methanol.

A sample of *Pichia pastoris* strains MSP10 and MSP12 harboring multiple copies of the spinach glycolate oxidase-encoding DNA under expression control of the AOX1 promoter, have been deposited under the terms of the Budapest Treaty with the Northern Regional Research Laboratories 24 Sep. 1992 and 28 Dec. 1992 respectively and are designated by the accession numbers NRRL Y-21001 and NRRL Y-21040, respectively.

Example 4

Expression of Glyolate Oxidase and Endogenous Catalase in MSP10 and MSP12

Transformants MSP10 and MSP12 harboring multiple copies of the glycolate oxidase gene were evaluated individually for the ability to co-express endogenous catalase with enzymatically-active glycolate oxidase.

Cells were grown in shaker flasks for about 48 hrs to an $A_{600}$ of 2–10 in YNB medium with 1% glycerol at 30° C. Cells were then pelleted and shifted to fresh YNB medium containing 0.5% methanol (for induction) and incubated at 30° C. for an additional 16–24 hrs. For analysis, extracts of cells were prepared by transferring 100 mg of wet cells (blotted to remove excess moisture) to 1 ml of 50 mM sodium phosphate pH 7.4, 0.1 mM PMSF, 1 mM EDTA, and 0.1 mM FMN and vortex mixing at high speed for 2 min in the presence of 1 g of 0.5 mm glass beads. Lysate was assayed for the presence of both catalase and glycolate oxidase.

Optionally, cultures were grown in 10 L fermenters with agitators for about 48 hrs. to an $A_{600}$ of 2–10 in YNB with 1% glycerol at 30° C. Cells were exposed to fresh medium containing 0.5% methanol (for induction) and allowed to incubate for an additional 6 hrs. Cells were then harvested and lysed as described above and the lysate assayed for the presence of both glycolate oxidase and endogenous catalase.

Glycolate oxidase was measured according to the method of Soda et al. as described above. Catalase activity was measured according to the method of Beers et al., *J. Biol. Chem.*, 195:133 (1952). In this method samples suspected of containing catalase are mixed with an excess of hydrogen peroxide and absorbance is measure on an ultraviolet spectrophotometer at a wavelength of 240 nm. Table I illustrates co-expressed catalase and glycolate oxidase activities.

TABLE I

| Strain | Hrs. Post-induction | GO activity | | Catalase activity | |
|---|---|---|---|---|---|
| | | IU/g Blotted cells | IU/mg Total Protein | IU/g Blotted cells | IU/g Total Protein |
| MSP10 | 22 | 158 | 7.3 | 91147 | 4220 |
| MSP12 | 22 | 180 | 5.7 | 123761 | 3904 |

As can be seen in Table I, both catalase and glycolate oxidase can be effectively co-expressed by the strains MSP10 and MSP12.

Example 5

Figure 6:
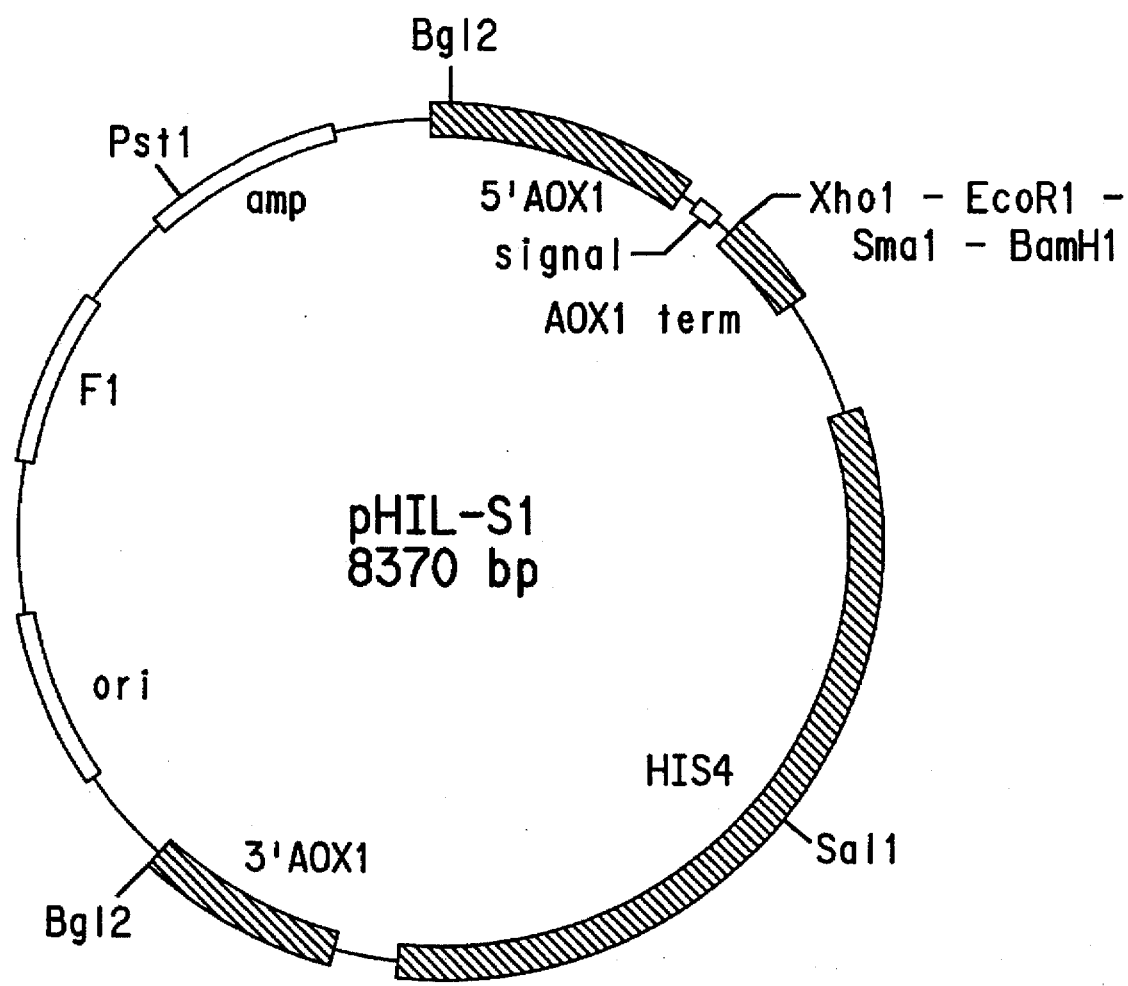
FIG. 6 is a plasmid map depicting plasmid pHIL-S1.

Secretion of Active Glycolate Oxidase by *Pichia pastoris* Construction of Transforming Secretion Vector A DNA fragment encoding GO as found in pDA-PCR#1 (FIG. 2) is amplified by polymerase chain reaction (PCR) as described in Example 1. Amplified GO DNA with appropriate termini is subcloned 5' to the PHO1 secretion signal sequence in pHIL-S1 by standard restriction endonuclease digestion followed by ligation with pHIL-S1 (FIG. 6). The result of this ligation will produce a vector capable of transforming a Pichia strain such as GTS115. Transformation of GTS115 is accomplished as described in Example 1.

Secretion of Active Glycolate Oxidase

Transformed cells are grown to saturation ($A_{600}$=10–20) in BMGY (0.1M potassium phosphate pH 6.0, 1.34%, 0.00004% biotin, 1% glycerol, 1% yeast extract, 2% peptone) at 30° C. (2–3 days). Cells are then harvested by centrifugation and resuspended in 1/20–1/10 volume of BMGY containing 0.5% methanol and minus glycerol. Cells are then incubated at 30° C., shaking for 1–4 days. Supernatant is analyzed for GO protein and/or GO activity by methods described in Example 3.

We claim:

1. A process for producing enzymatically-active glycolate oxidase, comprising the steps of:
   a. making a genetically stable, transformed methylotrophic yeast by
      i) introducing into a host methylotrophic yeast a heterologous nucleic acid which codes for enzymatically-active glycolate oxidase and which contains an antibiotic resistance gene, wherein said host methylotrophic yeast is selected from the group of methylotrophic yeast consisting of members of the genera Pichia, Hansenula, Torulopsis, Candida, and Karwinskia; and
      ii) selecting for the genetically stable, transformed methylotrophic yeast produced in step a.i) which is characterized by resistance to greater than 1 mg/mL concentration of antibiotic; and
   b. culturing said genetically stable, transformed methylotrophic yeast in a suitable medium under conditions which allow expression of said heterologous nucleic acid.

2. The process of claim 1 wherein said host methylotrophic yeast is a Pichia species.

3. The process of claim 1 further comprising recovering said transformed methylotrophic yeast.

4. A transformed methylotrophic yeast characterized by resistance to greater than 1 mg/mL concentration of antibiotic wherein the transformed methylotrophic yeast expresses enzymatically-active glycolate oxidase, the transformed methylotrophic yeast comprising multiple copies of a heterologous nucleic acid which codes for enzymatically active glycolate oxidase, the heterologous nucleic acid stably incorporated into the genome of a host methylotrophic yeast which is a species selected from the group of methylotrophic yeast species consisting of members of the genera Pichia, Hansenula, Torulopsis, Candida, and Karwinskia.

5. The genetically stable, transformed methylotrophic yeast strain of claim 4 wherein said heterologous nucleic acid codes for spinach enzymatically-active glycolate oxidase.

6. The genetically stable, transformed methylotrophic yeast of claim 4 wherein the host is a Pichia species.

7. The genetically stable, transformed methylotrophic yeast of claim 6 wherein the host is *Pichia pastoris*.

8. *Pichia pastoris* MSP10, which has been transformed with plasmid pMP1, expresses an enzymatically-active heterologous glycolate oxidase, and which has NRRL Number Y-21001.

9. *Pichia pastoris* MSP12, which has been transformed with plasmid pMP1, expresses an enzymatically-active heterologous glycolate oxidase, and has NRRL Number Y-21040.

10. A nucleic acid sequence comprising in a 5' to 3' direction of transcription a Pichia promoter operably joined to a DNA fragment derived from a plant encoding enzymatically active glycolate oxidase which is operably joined to a transcription termination regulatory region functional in Pichia.

11. The nucleic acid sequence of claim 10 wherein the promoter is an AOX promoter.

12. The nucleic acid sequence of claim 10 further comprising an AOX1 transcriptional termination element attached to the 3' end of said DNA fragment encoding enzymatically-active glycolate oxidase.

13. Plasmid pMP1 which is designated NRRL B-21292 and contains said nucleic acid sequence of claim 10.

14. A process for producing enzymatically-active glycolate oxidase according to claim 1 wherein the host methylotrophic yeast expresses enzymatically-active endogenous catalase.

15. The method of claim 2 wherein the enzymatically active glycolate oxidase is active within the genetically stable, transformed methylotrophic yeast.

16. The method of claim 1 wherein enzymatically active glycolate oxidase is produced at levels up to 1440 IU of active glycolate oxidase/gram dry cell weight.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 28 bases
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:1:

TACCGAATTC ATGGAGATCA CAAATGTG 28

( 2 ) INFORMATION FOR SEQ ID NO:2:

( i ) SEQUENCE CHARACTERISTICS:
( A ) LENGTH: 28 bases
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:2:

AACAGAATTC TTATAATCTG GCAACAGA ( 2 ) INFORMATION FOR SEQ ID NO:3:

( i ) SEQUENCE CHARACTERISTICS:
( A ) LENGTH: 369 amino acids
( B ) TYPE: amino acid
( C ) STRANDEDNESS: unknown
( D ) TOPOLOGY: unknown ( i i ) MOLECULE TYPE: protein ( x i ) SEQUENCE DESCRIPTION: SEQ ID NO:3:

| Met | Glu | Ile | Thr | Asn | Val | Asn | Glu | Tyr | Glu | Ala | Ile | Ala | Lys | Gln | Lys |
|---|---|---|---|---|---|---|---|---|---|---|---|---|---|---|---|
| 1 | | | | 5 | | | | | 10 | | | | | 15 | |

| Leu | Pro | Lys | Met | Val | Tyr | Asp | Tyr | Tyr | Ala | Ser | Gly | Ala | Glu | Asp | Gln |
|---|---|---|---|---|---|---|---|---|---|---|---|---|---|---|---|
| | | | 20 | | | | 25 | | | | | 30 | | | |

| Trp | Thr | Leu | Ala | Glu | Asn | Arg | Asn | Ala | Phe | Ser | Arg | Ile | Leu | Phe | Arg |
|---|---|---|---|---|---|---|---|---|---|---|---|---|---|---|---|
| | | 35 | | | | | 40 | | | | | 45 | | | |

| Pro | Arg | Ile | Leu | Ile | Asp | Val | Thr | Asn | Ile | Asp | Met | Thr | Thr | Thr | Ile |
|---|---|---|---|---|---|---|---|---|---|---|---|---|---|---|---|
| | 50 | | | | | 55 | | | | | 60 | | | | |

| Leu | Gly | Phe | Lys | Ile | Ser | Met | Pro | Ile | Met | Ile | Ala | Pro | Thr | Ala | Met |
|---|---|---|---|---|---|---|---|---|---|---|---|---|---|---|---|
| 65 | | | | | 70 | | | | | 75 | | | | | 80 |

| Gln | Lys | Met | Ala | His | Pro | Glu | Gly | Glu | Tyr | Ala | Thr | Ala | Arg | Ala | Ala |
|---|---|---|---|---|---|---|---|---|---|---|---|---|---|---|---|
| | | | | 85 | | | | | 90 | | | | | 95 | |

| Ser | Ala | Ala | Gly | Thr | Ile | Met | Thr | Leu | Ser | Ser | Trp | Ala | Thr | Ser | Ser |
|---|---|---|---|---|---|---|---|---|---|---|---|---|---|---|---|
| | | | 100 | | | | | 105 | | | | | 110 | | |

| Val | Glu | Glu | Val | Ala | Ser | Thr | Gly | Pro | Gly | Ile | Arg | Phe | Phe | Gln | Leu |
|---|---|---|---|---|---|---|---|---|---|---|---|---|---|---|---|
| | | 115 | | | | | 120 | | | | | 125 | | | |

| Tyr | Val | Tyr | Lys | Asp | Arg | Asn | Val | Val | Ala | Gln | Leu | Val | Arg | Arg | Ala |
|---|---|---|---|---|---|---|---|---|---|---|---|---|---|---|---|
| | 130 | | | | | 135 | | | | | 140 | | | | |

| Glu | Arg | Ala | Gly | Phe | Lys | Ala | Ile | Ala | Leu | Thr | Val | Asp | Thr | Pro | Arg |
|---|---|---|---|---|---|---|---|---|---|---|---|---|---|---|---|
| 145 | | | | | 150 | | | | | 155 | | | | | 160 |

| Leu | Gly | Arg | Arg | Glu | Ala | Asp | Ile | Lys | Asn | Arg | Phe | Val | Leu | Pro | Pro |
|---|---|---|---|---|---|---|---|---|---|---|---|---|---|---|---|
| | | | | 165 | | | | | 170 | | | | | 175 | |

| | | | | | | | | | | | | | | |
|---|---|---|---|---|---|---|---|---|---|---|---|---|---|---|
| Phe | Leu | Thr | Leu 180 | Lys | Asn | Phe | Glu | Gly 185 | Ile | Asp | Leu | Gly | Lys 190 | Met | Asp |
| Lys | Ala | Asn 195 | Asp | Ser | Gly | Leu | Ser 200 | Ser | Tyr | Val | Ala | Gly 205 | Gln | Ile | Asp |
| Arg | Ser 210 | Leu | Ser | Trp | Lys | Asp 215 | Val | Ala | Trp | Leu | Gln 220 | Thr | Ile | Thr | Ser |
| Leu 225 | Pro | Ile | Leu | Val | Lys 230 | Gly | Val | Ile | Thr | Ala 235 | Glu | Asp | Ala | Arg | Leu 240 |
| Ala | Val | Gln | His | Gly 245 | Ala | Ala | Gly | Ile | Ile 250 | Val | Ser | Asn | His | Gly 255 | Ala |
| Arg | Gln | Leu | Asp 260 | Tyr | Val | Pro | Ala | Thr 265 | Ile | Met | Ala | Leu | Glu 270 | Glu | Val |
| Val | Lys | Ala 275 | Ala | Gln | Gly | Arg | Ile 280 | Pro | Val | Phe | Leu | Asp 285 | Gly | Gly | Val |
| Arg | Arg 290 | Gly | Thr | Asp | Val | Phe 295 | Lys | Ala | Leu | Ala | Leu 300 | Gly | Ala | Ala | Gly |
| Val 305 | Phe | Ile | Gly | Arg | Pro 310 | Val | Val | Phe | Ser | Leu 315 | Ala | Ala | Glu | Gly | Glu 320 |
| Ala | Gly | Val | Lys | Lys 325 | Val | Leu | Gln | Met | Met 330 | Arg | Asp | Glu | Phe | Glu 335 | Leu |
| Thr | Met | Ala | Leu 340 | Ser | Gly | Cys | Arg | Ser 345 | Leu | Lys | Glu | Ile | Ser 350 | Arg | Ser |
| His | Ile | Ala 355 | Ala | Asp | Trp | Asp | Gly 360 | Pro | Ser | Ser | Arg | Ala 365 | Val | Ala | Arg |
| Leu | | | | | | | | | | | | | | | |